United States Patent
O'Malley

(10) Patent No.: US 9,554,973 B2
(45) Date of Patent: Jan. 31, 2017

(54) MICRO-ENCAPSULATION OF OZONATED OILS

(71) Applicant: Paul O'Malley, Sylmar, CA (US)

(72) Inventor: Paul O'Malley, Sylmar, CA (US)

( * ) Notice: Subject to any disclaimer, the term of this patent is extended or adjusted under 35 U.S.C. 154(b) by 0 days.

(21) Appl. No.: 15/227,769

(22) Filed: Aug. 3, 2016

(65) Prior Publication Data

US 2016/0338916 A1    Nov. 24, 2016

Related U.S. Application Data

(63) Continuation-in-part of application No. 15/198,221, filed on Jun. 30, 2016, which is a continuation of application No. 14/340,989, filed on Jul. 25, 2014, now Pat. No. 9,403,181.

(60) Provisional application No. 62/201,589, filed on Aug. 6, 2015, provisional application No. 61/859,135, filed on Jul. 26, 2013.

(51) Int. Cl.

| | |
|---|---|
| *A47K 5/12* | (2006.01) |
| *A61K 8/11* | (2006.01) |
| *A61Q 11/00* | (2006.01) |
| *A61K 8/92* | (2006.01) |
| *A61K 8/97* | (2006.01) |
| *A61K 8/34* | (2006.01) |
| *A61K 8/19* | (2006.01) |
| *A61K 8/23* | (2006.01) |
| *A61K 8/365* | (2006.01) |
| *A61K 8/66* | (2006.01) |
| *A61K 8/22* | (2006.01) |
| *A61K 8/20* | (2006.01) |
| *A61K 8/46* | (2006.01) |
| *A61K 8/60* | (2006.01) |
| *A61K 8/24* | (2006.01) |
| *A61K 35/747* | (2015.01) |
| *A61K 9/00* | (2006.01) |
| *A61K 35/744* | (2015.01) |
| *A61K 33/30* | (2006.01) |
| *A61K 35/00* | (2006.01) |

(52) U.S. Cl.
CPC . *A61K 8/11* (2013.01); *A61K 8/19* (2013.01); *A61K 8/20* (2013.01); *A61K 8/22* (2013.01); *A61K 8/23* (2013.01); *A61K 8/24* (2013.01); *A61K 8/345* (2013.01); *A61K 8/365* (2013.01); *A61K 8/463* (2013.01); *A61K 8/602* (2013.01); *A61K 8/66* (2013.01); *A61K 8/922* (2013.01); *A61K 8/97* (2013.01); *A61K 9/0056* (2013.01); *A61K 33/30* (2013.01); *A61K 35/744* (2013.01); *A61K 35/747* (2013.01); *A61Q 11/00* (2013.01); *A61K 2035/115* (2013.01); *A61K 2800/5922* (2013.01)

(58) Field of Classification Search
USPC .......................................... 424/49; 239/302
See application file for complete search history.

(56) References Cited

U.S. PATENT DOCUMENTS

| | | | | |
|---|---|---|---|---|
| 8,900,556 | B2 * | 12/2014 | Oxman | ................. A61K 6/083 424/423 |
| 2009/0117056 | A1 | 5/2009 | Hodal, Jr. | |
| 2012/0251512 | A1 | 10/2012 | Farmer | |
| 2013/0344010 | A1 | 12/2013 | Pompejus | |
| 2015/0030546 | A1 | 1/2015 | O'Malley | |
| 2015/0367366 | A1 * | 12/2015 | Edwards | .................. A23G 1/50 239/302 |

\* cited by examiner

*Primary Examiner* — Walter Webb
(74) *Attorney, Agent, or Firm* — Hackler Daghighian Martino & Novak

(57) ABSTRACT

A two-part oral care system includes a plurality of micro-encapsulated vessels containing an oxidative composition inside a coating, the oxidative composition having a pH less than 7.5, and a reductant composition, the reductant composition having a pH greater than 7. The micro-encapsulated vessels isolate the oxidative and reductant compositions from reacting with one another during storage and wherein the micro-encapsulated vessels can dispense when ruptured the oxidative and reductant compositions for combining to result in a final composition for use. The oxidative composition includes an ozonated oil comprising 0.01% to 5.0% per mass of the final composition and an oxidant comprising 0.01% to 2.0% per mass of the final composition. The reductant composition may include an aloe gel, xylitol, a ferrous sulfate, a sodium bicarbonate, a calcium carbonate, a zinc gluconate, a salt, a bromelain, a papain, and at least one essential oil.

17 Claims, No Drawings

MICRO-ENCAPSULATION OF OZONATED OILS

CROSS-REFERENCE TO RELATED APPLICATIONS

This non-provisional application claims priority to provisional application 62/201,589 filed on Aug. 6, 2015, the entire contents of which are fully incorporated herein with this reference. This continuation-in-part application claims priority to application Ser. No. 15/198,221 filed on Jun. 30, 2016, which itself was a continuation application which claimed priority to application Ser. No. 14/340,989 filed on Jul. 25, 2014, which itself claimed priority to provisional application 61/859,135 filed on Jul. 26, 2013, the contents of which all applications are fully incorporated herein with these references.

DESCRIPTION

Field of the Invention

The present invention generally relates to ozonated oils. More particularly, the present invention relates to micro-encapsulation of ozonated oils.

Background of the Invention

Ozonated plant oils have been shown to have a number of pharmaceutical properties, from anti-microbial, to promoting and accelerating tissue healing and improving the oxygenation of tissue where applied. Therefore, there is a need for ozonated oils to be in the form of a micro-encapsulated ozonated oil such that its affects can be spread further. Therefore, the aim is then to formulate a new range of products containing organic ozonated plant oils in micro-capsules.

The proposed mix will improve health, with specific emphasis on oral health benefits to reduced oral disease and its known effect into general health. The taste of products containing micro-encapsulated ozonated oils will be improved as there will be no initial direct contact with ozonated oils. Micro-encapsulates could be incorporated into dental floss, tooth brush bristles, chewing sticks, comforters, denture bases, plastic retainers, orthodontic devices. In time the products can be extended into other markets, for example animal welfare and treating large animal disease.

SUMMARY OF THE INVENTION

An exemplary embodiment of the present invention is a two-part oral care system, which includes a plurality of micro-encapsulated vessels containing an oxidative composition inside a coating, the oxidative composition having a pH less than 7.5, and a reductant composition, the reductant composition having a pH greater than 7. The micro-encapsulated vessels isolate the oxidative and reductant compositions from reacting with one another during storage and wherein the micro-encapsulated vessels can dispense when ruptured the oxidative and reductant compositions for combining to result in a final composition for use. The oxidative composition may include: an ozonated oil comprising 0.01% to 5.0% per mass of the final composition and an oxidant comprising 0.01% to 2.0% per mass of the final composition. The reductant composition may comprise all or just any one of the following or any combination of the following: an aloe gel or aloe vera comprising 0.01% to 25.0% per mass of the final composition; a xylitol comprising 0.1% to 60.0% per mass of the final composition; a ferrous sulfate comprising 0.0001% to 0.1% per mass of the final composition; a sodium bicarbonate comprising 0.01%-6.0% per mass of the final composition; a calcium carbonate comprising 1.0%-40.0% per mass of the final composition; a zinc gluconate comprising 0.01%-3.0% per mass of the final composition; a salt comprising 0.01%-3.0% per mass of the final composition; a bromelain comprising 0.01%-3.0% per mass of the final composition; a papain comprising 0.01%-3.0% per mass of the final composition; and at least one essential oil comprising 1.0 to 3.5% per mass of the final composition. The oxidative composition and the reductant composition comprise 100.0% per mass of the final composition.

In other exemplary embodiments, the ozonated oil may be olive oil, grapeseed oil, hempseed oil or avocado oil wherein the oil is infused with ozone.

In other exemplary embodiments, the oxidant may include hydrogen peroxide or chlorine dioxide.

In other exemplary embodiments, the oxidative composition further may include calcium citrate comprising 0.01% to 3.0% per mass of the final composition.

In other exemplary embodiments, the salt may be a sea salt.

In other exemplary embodiments, the sea salt may be a kosher flake sea salt, a fine sonoma sea salt or a pink himalayan sea salt.

In other exemplary embodiments, a surfactant may be added to either the oxidative composition or the reductant composition, the surfactant comprising 0.5% to 3.0% per mass of the final composition.

In other exemplary embodiments, the surfactant may be sodium coco sulfate or sodium decylglucoside.

In other exemplary embodiments, the reductant composition may comprise a nano particle silver water comprising 0.1% to 10.0% per mass of the final composition.

In other exemplary embodiments, the reductant composition may comprise a hydroxyapatite comprising 0.1% to 4.0% per mass of the final composition.

In other exemplary embodiments, the oxidative composition may comprise a pH equal to or between 6.3 to 7.5.

In other exemplary embodiments, the at least one essential oil may be selected from the group consisting of eucalyptol, mentol and thymol.

In other exemplary embodiments, the plurality of micro-encapsulated vessels containing the oxidative composition may be suspended within the reductant composition.

In other exemplary embodiments it may include a probiotic lozenge to be used after the final composition, the probiotic lozenge comprising: i.) *lactobacillus acidophilus* comprising 15.0% to 40.0% per mass of the probiotic lozenge; ii.) *lactobacillus reuteri* comprising 5.0% to 20.0% per mass of the probiotic lozenge; iii.) *lactobacillus salivarius* comprising 5.0% to 20.0% per mass of the probiotic lozenge; iv.) *lactobacillus paracasei* comprising 5.0% to 20.0% per mass of the probiotic lozenge; v.) *streptococcus thermophiles* comprising 5.0% to 20.0% per mass of the probiotic lozenge; vi.) *streptococcus salivarius* BLIS K-12 comprising 5.0% to 30.0% per mass of the probiotic lozenge; vii.) *streptococcus salivarius* BLIS M-18 comprising 5.0% to 30.0% per mass of the probiotic lozenge; viii.) zinc oxide comprising 0.2% to 5.0% per mass of the probiotic lozenge; ix.) hydroxyapatite comprising 0.1% to 25.0% per mass of the probiotic lozenge; and x.) dicalcium phosphate comprising 0.1% to 5.0% per mass of the probiotic lozenge.

In other exemplary embodiments, the probiotic lozenge may further include *lactobacillus brevis* comprising 5.0% to 20.0% per mass of the probiotic lozenge.

In other exemplary embodiments, the coating may comprise ethyl cellulose, polyvinyl alcohol, gelatin, sodium alginate or an agar-based sugar polymer.

In other exemplary embodiments, the ozonated oil may comprise 0.01% to 5.0% per mass of the final composition is in a diluted form, the dilution percentage being 0.1%, 0.2%, 0.4%, 0.75%, 1%, 5%, 10%, 25% or 50% from a 100% non-diluted ozonated oil.

Other features and advantages of the present invention will become apparent from the following more detailed description, when taken in conjunction with the accompanying drawings, which illustrate, by way of example, the principles of the invention.

DETAILED DESCRIPTION OF THE PREFERRED EMBODIMENTS

One aim is to formulate a new range of products containing organic ozonated plant oils in micro-capsules, with a water-based paste for oral hygiene. The proposed mix will improve oral health and overall health benefits to longevity and reduced oral disease. The taste will be improved as there would be no initial direct contact with ozonated oils. Micro-encapsulates could be incorporated into dental floss, tooth brush bristles, chewing sticks, comforters, denture bases, plastic retainers, orthodontic devices. It would be able to then extend the product range into other markets, for example animal welfare and treating large animal disease. Other products are ripe for commercialization; for example, wound plasters, wound dressings, creams (for herpes, shingles, acne).

The concept of micro-encapsulation is not new to pharmaceuticals. Micro-encapsulation allows different additives in a mix to be kept separate. If additives were simply mixed together, the additives could chemically react with each other and any pharmaceutical activity would be lost or the product be degraded within a short time. The IUPAC definition of a micro-capsule is a "Hollow micro-particle composed of a solid shell surrounding a core-forming space available to permanently or temporarily entrapped substances." The "entrapped substances" can be drugs, pesticides, dyes, etc.

Micro-encapsulation is a process in which tiny particles or droplets are surrounded by a coating to give small capsules of many useful properties. In general, it is used to incorporate food ingredients, enzymes, cells or other materials on a micro metric scale. Micro-encapsulation can also be used to enclose solids, liquids, or gases inside a micro-metric wall made of hard or soft soluble film, in order to reduce dosing frequency and prevent the degradation of pharmaceuticals. In a relatively simple form, a micro-capsule is a small sphere with a uniform wall around it. The material inside the micro-capsule is referred to as the core, internal phase, or fill, whereas the wall is sometimes called a shell, coating, or membrane.

Some materials like lipids and polymers, such as alginate, may be used as a mixture to trap the material of interest inside. Most micro-capsules have diameters between a few micrometers and a few millimeters. The coating materials generally used for coating are: ethyl cellulose, polyvinyl alcohol, gelatin and/or sodium alginate.

The reasons for micro-encapsulation are countless. It is mainly used to increase the stability and life of the product being encapsulated, and also to facilitate the manipulation of the product and control its liberation in an adequate time and space. In some cases, the core must be isolated from its surroundings, as in isolating vitamins from the deteriorating effects of oxygen, retarding evaporation of a volatile core, improving the handling properties of a sticky material, or isolating a reactive core from chemical attack. In other cases, the objective is not to isolate the core completely but to control the rate at which it leaves the micro-capsule, as in the controlled release of drugs or pesticides. The problem may be as simple as masking the taste or odor of the core, or as complex as increasing the selectivity of an adsorption or extraction process. In environmental science, a pesticide may be micro-encapsulated to minimize leaching or volatilization risks.

In this application, the stability of the organic ozonoid will be at risk were it to come into contact with any water-phase of the additional product components. There are a number of ways to isolate different product components, so the end product is activated as required. Examples of this is a multiple-barreled syringe with a mixing tip that mixes the components when the product is dispensed. Another example is a tube with multiple compartments where the product is equally mixed on extrusion—e.g. toothpaste. But both these "solutions" have associated problems as product can leak from one side to another setting up a chemical reaction that degrades the end product and any potential pharmaceutical effect is lost.

Micro-encapsulation offers a unique way to solve this issue, as multiple ingredients can be encapsulated either individually or in combination in each micro-capsule, and in this example, the mechanical action of tooth brushing will rupture the micro-capsules, releasing the active ingredients for maximum effect. It is important that the encapsulated ingredients do not react with the capsule wall or pose a health risk to any individual. Micro-encapsulation also allows a long shelf life for products that otherwise would have a short-term storage issue.

One might ask what ingredient will it be encapsulated with, or whether it will be vegan/gluten free, or synthetic or natural. One solution of the present invention micro-encapsulated cover is to use a sugar polymer based on agar. It's a cross synthetic-natural cover and used by the main pharmaceuticals worldwide. It is vegan, gluten free and acceptable by all religious groups. It dries in milliseconds to form the droplets and it breaks down only on trauma to the encapsulate coat. Also, it can withstand the mixing dynamics with other products.

One might ask how long the micro-encapsulated structure will be stable. In one exemplary embodiment the answer is indefinitely, provided the micro-encapsulate is not "traumatized."

One might ask will it still create a strong taste. An exemplary embodiment of the present invention will have no taste or active components in terms of the ozonated oils until the micro-capsules containing the ozonated oils are broken to release them. For example, in one embodiment, the product may be in a toothpaste. The action of brushing the paste containing the micro-encapsulates will fracture the micro-capsules, releasing the ozonated oils, and the contact with oral fluid will result in the ozonated oils breaking down to release hydrogen peroxide via the Criege Reaction.

One skilled in the art of micro-encapsulation might ask whether we should we use avocado. One embodiment of the present invention may prefer to use avocado, as out of all the ozonated oils available, ozonated avocado oil has the least offensive taste.

One might ask, what percentage (%) would then be highly effective in the formula? There will be a balance between efficacy and taste on brushing. Once more micro-biological tests are back, these results will point towards a band of concentration efficacy. Ozonated avocado oil was sent to Professor Anil Chuturgoon, KZN for H1 NMR and micro-biological testing. 100ml samples at dilutions of 0.1%, 0.2%, 0.4%, 0.75%, 1%, 5%, 10%, 25%, 50%, 100% ozonated avocado oil, diluted from the non-ozonated original oil, are being tested. The various ozonated oil concentrations will be tested against the following common oral bacteria; i. N11060, ii. *Treponema denticola*, iii. *Porphyromonas gingivalis*, iv. *Actinobacillus actinomycetemcomitans*, v. *Bacteroides forsythus*, vi. *Streptococcus mutans*, vii. *Actinomyces viscosus*, viii. *Prevotella intermedia*.

In the present embodiment, it is a dilution of only 0.2% due to flavor challenges. With micro-encapsulation the concentration could be increased to make the paste more effective, thus the testing of the other various dilutions. It is understood by those skilled in the art that the various dilution percentages presented herein could all work for the present invention.

The method of micro-encapsulation involves formulating a mixture or emulsion of oils and polysaccharides, which is then aerosoled and "freeze-dried" leading to a fine dry micro-encapsulated particle formation.

There may be a problem, as water based emulsion of oils and polysaccharides and its resultant micro-encapsulate needs to be evaluated, as 7. The system of claim 1, including a surfactant added to either the oxidative composition or the reductant composition, the surfactant comprising 0.5% to 3.0% per mass of the final composition.

8. The system of claim 7, wherein the surfactant comprises sodium coco sulfate or sodium decylglucoside.

9. The system of claim 1, wherein the reductant composition comprises a nano particle silver water comprising 0.1% to 10.0% per mass of the final composition.

10. The system of claim 1, wherein the reductant composition comprises a hydroxyapatite comprising 0.1% to 4.0% per mass of the final composition.

11. The system of claim 1, wherein the oxidative composition comprises a pH equal to or between 6.3 to 7.5.

12. The system of claim 1, wherein the at least one essential oil is selected from the group consisting of eucalyptol, mentol and thymol.

13. The system of claim 1, wherein the plurality of micro-encapsulated vessels containing the oxidative composition are suspended within the reductant composition.

14. The system of claim 1, further including a probiotic lozenge to be used after the final composition, the probiotic lozenge comprising:
   i.) *lactobacillus acidophilus* comprising 15.0% to 40.0% per mass of the probiotic lozenge;
   ii.) *lactobacillus reuteri* comprising 5.0% to 20.0% per mass of the probiotic lozenge;
   iii.) *lactobacillus salivarius* comprising 5.0% to 20.0% per mass of the probiotic lozenge;
   iv.) *lactobacillus paracasei* comprising 5.0% to 20.0% per mass of the probiotic lozenge;
   v.) *streptococcus thermophiles* comprising 5.0% to 20.0% per mass of the probiotic lozenge;
   vi.) *streptococcus salivarius* BLIS K-12 comprising 5.0% to 30.0% per mass of the probiotic lozenge;
   vii.) *streptococcus salivarius* BLIS M-18 comprising 5.0% to 30.0% per mass of the probiotic lozenge;
   viii.) zinc oxide comprising 0.2% to 5.0% per mass of the probiotic lozenge;
   ix.) hydroxyapatite comprising 0.1% to 25.0% per mass of the probiotic lozenge; and
   x.) dicalcium phosphate comprising 0.1% to 5.0% per mass of the probiotic lozenge.

15. The system of claim 14, wherein the probiotic lozenge further includes *lactobacillus brevis* comprising 5.0% to 20.0% per mass of the probiotic lozenge.

16. The system of claim 1, wherein the coating comprises ethyl cellulose, polyvinyl alcohol, gelatin, sodium alginate or an agar-based sugar polymer.

17. The system of claim 1, wherein the ozonated oil comprising 0.01% to 5.0% per mass of the final composition is in a diluted form, the dilution percentage being 0.1%, 0.2%, 0.4%, 0.75%, 1%, 5%, 10%, 25% or 50% from a 100% non-diluted ozonated oil.

* * * * *